United States Patent [19]

Sobotta

[11] Patent Number: 5,488,136
[45] Date of Patent: Jan. 30, 1996

[54] PROCESS FOR THE RACEMIZATION OF NONRACEMIC 3-OXYOCYLOPENTANE- OR -HEXANECARBOXYLIC ACIDS OR THEIR ESTERS WITH $C_1$-$C_6$-ALCOHOLS

[75] Inventor: Rainer Sobotta, Ingelheim, Germany

[73] Assignee: Boehringer Ingelheim KG, Ingelheim am Rhein, Germany

[21] Appl. No.: 971,775

[22] PCT Filed: Jul. 31, 1991

[86] PCT No.: PCT/EP91/01434

§ 371 Date: Apr. 16, 1993

§ 102(e) Date: Apr. 16, 1993

[87] PCT Pub. No.: WO92/02483

PCT Pub. Date: Feb. 29, 1992

[30] Foreign Application Priority Data

Aug. 4, 1990 [DE] Germany ............ 40 24 836.4

[51] Int. Cl.[6] ............................................. C07C 69/74

[52] U.S. Cl. ............... 560/122; 560/126; 562/504; 562/508

[58] Field of Search ................. 560/122, 126; 562/504, 508

[56] References Cited

PUBLICATIONS

Abstract to JP, A, 6446, 01 Jan 1989, Azumai, T.

*Primary Examiner*—José G. Dees
*Assistant Examiner*—Dwayne C. Jones
*Attorney, Agent, or Firm*—R. P. Raymond; A. R. Stempel; M-E. M. Devlin

[57] ABSTRACT

Racemates are obtained from non-racemic 3-oxocyclopentane or 3-oxocyclohexane carboxylic acids or their esters by esterification and ketalization of the non-racemic acid with orthoformic acid ester in an alocohol, racemization and hydrolysis of the product obtained with an alcoholate and isolation of the racemate.

8 Claims, No Drawings

PROCESS FOR THE RACEMIZATION OF NONRACEMIC 3-OXYOCYLOPENTANE- OR -HEXANECARBOXYLIC ACIDS OR THEIR ESTERS WITH $C_1$-$C_6$-ALCOHOLS

The invention relates to a new process by which nonracemic 3-oxocyclopentane- or 3-oxocyclohexanecarboxylic acids or their esters with lower alcohols can be racemized to the corresponding racemic acids or esters.

Pure enantionmers of 3-oxocycloalkanecarboxylic acids are required e.g. for the production of hetrazepines which can be used as drugs. As during the synthesis of those acids racemates are formed a resolution of the racemates is necessary. In order that also the unsuitable enantiomer can be utilized it has to be racemized and then be subjected to resolution of racemate.

The invention solves the problem to convert enantiomers or nonracemic mixtures of enantiomers of 3-oxocycloalkanecarboxylic acids or of their esters with lower alcohols into the racemates.

In this manner particularly the unsuitable enantiomers or nonracemic mixtures of enantiomers remaining after the resolution of the racemates mentioned above can be processed into a useful product.

Racemization of nonracemic 3-oxocycloalkanecarboxylic acids or their esters is not possible by usual methods e.g. by treatment with bases because condensation products are formed.

It has now be found a process by means of which enantiomeres or nonracemic mixtures of enantiomers of 3-oxocyclopentane- or 3-oxocyclohexanecarboxylic acids or of their $C_1$–$C_6$-alkyl esters can surprisingly be transformed into the corresponding racemates.

The process is characterized in that the enantiomer or the nonracemic mixture of enantiomers is first esterified in an alcohol with an orthoformic acid lower alkyl ester in the presence of a catalytical amount of a strong acid (if the starting material is not yet an ester) and then ketalized, the resulting product is racemized by means of an alcoholate and subsequently hydrolized to form the racemic acid or the racemic ester followed by isolating of the racemic compounds according to usual methods.

The steps of the process are advantageously performed without isolation of intermediates.

The alcohol to be used is an aliphatic alcohol with 1–6 C-atoms, preferably methanol, ethanol, propanol. It is prefered to use orthoformic acids and alcoholates derived from the same alcohol which is used as reaction medium.

As catalysts there are used the acids usual for these purposes (strong mineral acids such as sulfuric acid, hydrochloric acid, toluene sulfonic acid, methane sulfonic acid).

The manufacture of the ketals is carried out preferably at the boiling temperature of the reaction mixture. The hydrolysis of the ketal group (to form the ester) is carried out at room temperature or with cooling. If the ester group shall be hydrolized too this is carried out under reflux temperature.

An example for carrying out each of the process variants which the expert, if desired, can easily modify will now be given.

EXAMPLE 1

Racemic methyl-3-oxocyclopentanecarboxylate 318.36 g (3 mol) of trimethylorthoformate are added gradually to a solution of 128.2 g (1 mol) of nonracemic 3-oxocyclopentanecarboxylic acid and 11.4 g (0.06 mol) of p-toluene sulfonic acid hydrate in 380 ml of methanol within 5–10 minutes while stirring, The mixture is heated and during 25 minutes a mixture of formic acid methyl ester and methanol is distilled off (about 185 g of distillate), Thereafter 29 g of 30% sodium methylate solution (0.16 mol) are added and the reaction mixture is kept boiling under reflux for 2 hours; methanol is distilled off, the residue cooled to 10° C. and dissolved by adding 230 ml of methylene chloride and 200 ml of water. By adding 5% sulfuric acid the mixture is adjusted to pH 1.4 and stirred at 10° C. for 30 minutes. The methylene chloride phase is separated and the aqueous phase extracted again with 100 ml of methylene chloride. The combined organic phases are stirred with 50 ml of water, separated and the solvent is distilled off in vacuo. The residue is fractionated in vacuo.

Main fraction: 13.4 g; $bp_{23\ mbar}$: 110° C.; 92% of theory. In a polarimeter a sample showed an angle of rotation of 0°.

EXAMPLE 2

Racemic 3-Oxocyclohexanecarboxylic acid

As described in Example 1 7.11 g (0.05 mol) of nonracemic 3-oxocyclohexanecarboxylic acid are racemized with 18.9 g (0.178 mol) of trimethylorthoformate in the presence of 30% sodium methylate solution.

The hydrolysis to form the racemic keto acid is carried out after distilling off the solvent. There are added 85 g of 2N hydrochloric acid to the residue and the mixture is kept boiling under reflux for 6 hours. Subsequently concentration to a residue of 21 g takes place in vacuo and after cooling the residue is extracted once with 50 ml and twice with 20 ml of chloroform. From the combined organic phases the solvent is removed in vacuo. A sample of the residue did not show an angle of rotation in a polarimeter.

Yield: 6.7 g ( 94.2% of theory).

I claim:

1. A process for the racemization of non-racemic 3-oxocyclopentanecarboxylic acid and 3-oxocyclohexanecarboxylic acid and their corresponding esters with $C_1$–$C_6$ alcohols which comprises:

a) esterifying starting acid material with an orthoformic acid ester of a $C_1$–$C_6$ alcohol in the presence of a catalytical amount of a strong acid;

b) ketalizing the resulting ester with an orthoformic acid ester of a $C_1$–$C_6$ alcohol in the presence of a strong acid;

c) racemizing the resulting ketal by means of a sodium or potassium alkoxide of a $C_1$–$C_6$ alcohol;

d) hydrolysing the resulting material by treatment with dilute acid to form the racemic acid; and e) isolating the resulting racemic acid or the resulting racemic ester.

2. The process as recited in claim 1 wherein the $C_1$–$C_6$ alcohol is $C_1$–$C_3$ alcohol.

3. The process as recited in claim 2 wherein the $C_1$–$C_3$ alcohol is methanol or ethanol.

4. The process as recited in claim 1 wherein the hydrolysis is carried at boiling temperature.

5. A process for the racemization of non-racemic esters of 3-oxocyclopentanecarboxylic acid and 3-oxocyclohexanecarboxylic acid with $C_1$–$C_6$ alcohols which comprises:

a) ketalizing the starting ester material with an orthoformic acid ester of a $C_1$–$C_6$ alcohol in the presence of a strong acid;

b) racemizing the resulting ketal by means of a sodium or potassium alkoxide of a $C_1$–$C_6$ alcohol;

c) hydrolysing the resulting material by treatment with dilute acid to form the racemic ester; and d) isolating the resulting racemic ester.

6. The process as recited in claim 5 wherein the $C_1$–$C_6$ alcohol is $C_1$–$C_3$ alochol.

7. The process as recited in claim 6 wherein the $C_1$–$C_3$ alcohol is methanol or ethanol.

8. The process as recited in claim 5 wherein the hydrolysis is carried at room temperature or with slight cooling to form the racemic ester.

\* \* \* \* \*